US010080708B2

(12) United States Patent
Peez et al.

(10) Patent No.: US 10,080,708 B2
(45) Date of Patent: Sep. 25, 2018

(54) GLASS IONOMER CEMENT, PROCESS OF PRODUCTION AND USE THEREOF (71) Applicant: 3M INNOVATIVE PROPERTIES COMPANY, St. Paul, MN (US)

(72) Inventors: Robert Peez, Landsberg (DE); Peter Braun, Penzing (DE); Markus Mikulla, Andechs-Frieding (DE); Rainer Guggenberger, Herrsching (DE)

(73) Assignee: 3M Innovative Properties Company, St. Paul, MN (US)

( * ) Notice: Subject to any disclaimer, the term of this patent is extended or adjusted under 35 U.S.C. 154(b) by 66 days.

(21) Appl. No.: 15/102,483

(22) PCT Filed: Dec. 8, 2014

(86) PCT No.: PCT/US2014/069042
§ 371 (c)(1),
(2) Date: Jun. 7, 2016

(87) PCT Pub. No.: WO2015/088956
PCT Pub. Date: Jun. 18, 2015

(65) Prior Publication Data
US 2016/0310368 A1 Oct. 27, 2016

(30) Foreign Application Priority Data
Dec. 12, 2013 (EP) ..................... 13196808

(51) Int. Cl.
*A61K 6/00* (2006.01)
*A61K 6/083* (2006.01)
(52) U.S. Cl.
CPC .......... *A61K 6/0835* (2013.01); *A61K 6/0008* (2013.01); *A61K 6/0073* (2013.01); *A61K 6/0088* (2013.01)

(58) Field of Classification Search
None
See application file for complete search history.

(56) References Cited

U.S. PATENT DOCUMENTS

| 3,629,187 | A | * | 12/1971 | Waller | ................ | A61K 6/0017 260/998.11 |
| 4,209,434 | A | | 6/1980 | Wilson | | |
| 4,360,605 | A | | 11/1982 | Schmitt | | |
| 4,376,835 | A | | 3/1983 | Schmitt | | |

(Continued)

FOREIGN PATENT DOCUMENTS

| EP | 0329268 A2 | * | 8/1989 | ........... A61K 6/0835 |
| EP | 0694298 | | 1/1996 | |

(Continued)

OTHER PUBLICATIONS

International Search Report for PCT International Application No. PCT/US2014/069042 dated Mar. 6, 2015, 4 pages.

(Continued)

*Primary Examiner* — Peter A Salamon (57) ABSTRACT

The invention relates to a kit of parts for preparing a glass ionomer cement, the kit comprising a Part A and a Part B, Part A being a powder and comprising an acid-reactive filler in an amount above about 60 wt. %, the acid-reactive filler having a mean particle size in the range of 3.5 to 10 μm, an non acid-reactive filler in an amount above about 1 wt. %, the non acid-reactive filler having a mean particle size in the range of 1.0 to 3.5 μm, Part A not comprising a polyacid in an amount above about 1 wt. %, wt. % with respect to the weight of Part A, Part B being a liquid and comprising a polyacid in an amount above about 30 wt. %, water, a complexing agent, wt. % with respect to the weight of Part B. The invention also relates to a process of producing a hardenable or hardening composition and use thereof in the dental field.

20 Claims, 1 Drawing Sheet (56) References Cited

U.S. PATENT DOCUMENTS

| | | | |
|---|---|---|---|
| 4,569,954 A * | 2/1986 | Wilson | A61K 6/0017 |
| | | | 106/35 |
| 4,738,722 A | 4/1988 | Ibsen | |
| 4,941,751 A | 7/1990 | Muhlbauer | |
| 5,318,929 A | 6/1994 | Jana | |
| 5,520,922 A * | 5/1996 | Gasser | A61K 6/0032 |
| | | | 424/422 |
| 5,922,785 A * | 7/1999 | Waller | A61K 6/0088 |
| | | | 433/228.1 |
| 6,355,585 B1 | 3/2002 | Suzuki | |
| 6,543,611 B1 | 4/2003 | Peuker | |
| 6,719,834 B1 | 4/2004 | Braun | |
| 8,083,844 B2 | 12/2011 | Arita | |
| 2003/0087986 A1 | 5/2003 | Mitra | |
| 2004/0192433 A1 | 9/2004 | Johnson | |
| 2007/0254998 A1 * | 11/2007 | Orlowski | A61K 6/0023 |
| | | | 524/425 |

FOREIGN PATENT DOCUMENTS

| | | |
|---|---|---|
| EP | 0783872 | 9/2003 |
| EP | 2011469 | 1/2009 |
| JP | 2796461 | 9/1998 |
| JP | 2002-275017 | 9/2002 |
| JP | 2012-6896 | 1/2012 |
| JP | 2013-40137 | 2/2013 |
| WO | WO 2012-101432 | 8/2012 |

OTHER PUBLICATIONS

Cotton et al., p. 949, *Advanced Inorganic Chemistry*, $3^{rd}$ Ed., Interscience Publishers, New York, New York, 1972, 3 pages.

* cited by examiner

GLASS IONOMER CEMENT, PROCESS OF PRODUCTION AND USE THEREOF

FIELD OF THE INVENTION

The invention relates to a dental composition curing by a glass ionomer cement reaction (GIZ) with improved storage stability having adequate physical properties, wherein the cement is obtainable by mixing a powder and liquid component or part.

BACKGROUND ART

Glass ionomer cements have been used for more than 30 years for dental restorative treatments. Typically glass ionomer cements are reacted by mixing a powder part with a liquid part. The powder component typically comprises as essential or important component an acid-reactive filler (e.g. a fluoro alumino silicate glass). The liquid component typically comprises as essential or important components water, polycarboxylic acid and a complexing agent (e.g. tartaric acid) for adjusting the setting properties. Main advantages of glass ionomer cements are self-adhesion to tooth structure, fluoride release and the ability to be placed in one part (bulk-fill). The main disadvantage is the brittle nature and relatively low physical-mechanical properties compared to resin-based composite filling materials. Hence there have been various approaches to improve the latter, especially the flexural strength.

It was found that by increasing the overall content of polycarboxylic acid in comparison to the acid-reactive filler, the flexural strength could be improved. However, by increasing the amount of polycarboxylic acid contained in the liquid part, the liquid part became too viscous making it nearly impossible to adequately mix the powder and liquid component. To overcome this issue, a part of the polycarboxylic acid was put in dry form into the powder component. By doing this, however, it was realized that the storage stability of the product is negatively affected. Over time, humidity being present in the air starts to migrate into the powder component causing a glass ionomer reaction to start at least partially.

In order to circumvent the susceptibility of the powder part to ambient humidity, encapsulating at least parts of the powder component was considered. It was also considered to add desiccants to the powder part. Another approach was to package the final product or at least the powder part into a humidity tight foil blister. This kind of packaging, however, is quite expensive and produces waste after use, which is not desired. Encapsulating particles is often not easy and may affect the overall reactivity of the encapsulated powder. The same holds true for adding a desiccant. Thus, there is still room for improvement especially with regard to the requirements to be fulfilled with respect to modern dental materials. Some of the materials are not sufficiently storage stable or require the material to be stored under special conditions, e.g. by sealing the material in expensive packaging materials.

U.S. Pat. No. 4,376,835 (Schmitt et al.) describes a calcium aluminium fluorosilicate glass powder, wherein the calcium in the surface of the powder's particles is depleted. The glass powder may be prepared by surface treating calcium aluminium fluorosilicate powder particles with an acid which forms calcium salts, washing the calcium salts off the treated particles and drying the washed particles. Cements formed from the glass powder exhibit reduced periods of water sensitivity, while permitting sufficient time of processing.

U.S. Pat. No. 6,719,834 (Braun et al.) relates to a polyelectrolyte cement containing at least two reaction partners: a) at least one metal-cation-releasing compound and b) one or more polyelectrolyte capable of being converted into a solid state, wherein at least one of the polyelectrolytes is at least partially water soluble and wherein at least a part of the reaction partners (a) and/or (b) is coated with an organic surface-coating agent. The polyelectrolyte cement is stable in storage and can be easily mixed.

WO 2012/101432 relates to a mixture of a glass ionomer cement and zinc phosphate. Preferably, the composition comprises 40-95% by weight of fluorosilicate glass and 5-60% by weight of zinc oxide as acid-reactive components. The compositions are for use in the repair of human hard tissue, in particular as dental restorative materials and in orthopaedic surgery.

EP 2 011 469 describes a composition where hydroxyl apatite is added as a reactive component to glass ionomer cements.

EP 0 694 298 relates to the use of a preformed glass ionomer filler which comprises a powdery reaction product between a polyalkenoic acid and a fluoride glass. This filler can release fluoride ions. Whereas most examples refer to the use of the filler in resin containing, light-curing dental composition, there is also an example using this preformed glass ionomer in a carboxylate cement with Zinc oxide and Magnesium oxide as basic ingredients. Yet no examples were found with regards to the use of the pre-formed glass ionomer filler in conventional glass ionomers. Also it has to be understood, that the production of such a pre-formed glass ionomer fillers comprises several steps.

U.S. Pat. No. 5,318,929 discloses an apatite-containing glass ceramic, which can be used in particular in forming glass ionomer cement and biomaterials which improves manipulability and adhesion vis-a-vis known technical solutions of glass ionomer cements.

U.S. Pat. No. 4,738,722 describes a buffered glass ionomer cement for dental use, which contains as fillers fluoro boro phosphoro calcium alumino silicate, zinc oxide (5-20%) and titanium dioxide in place of about half the amount of zinc oxide.

U.S. Pat. No. 6,355,585 discloses a glass powder for glass ionomer cement having high mechanical strength, containing a glass powder for glass ionomer cement having a shape in which a major axis length is from 3 to 1,000 times a minor axis length, in a glass powder for glass ionomer cement. The composition of the glass powder described refers to an acid reactive fluoro alumino silicate glass.

U.S. Pat. No. 8,083,844 describes the use of hydroxyl apatite as filler in glass ionomer cements.

JP 2002-275017 (Noritake) describes a material for preparing dental glass ionomer cements. The powdery material comprises 10-50 wt.-% of fluoroaluminosilicate glass powder, less or equal than 10 wt.-% of a powder selected from certain oxides, with the balance of a powdery inert filler. Due to a reduced content of fluoroaluminosilicate glass powder (10 to 50 wt.-%), the glass ionomer cement is said to be excellent in temporarily adhesive and temporarily sealing use, i.e. has reduced mechanical properties. Compressive strength values in the range of less than 70 MPa are reported.

U.S. Pat. No. 5,520,922 (Gasser et al.) relates to a filling material for dental root canals comprising (A) 25-80 wt.-% glass ionomer cement containing (a) an aluminium fluorosilicate glass, (b) a certain polymeric polyacid, (c) water and (B) 25-75 wt.-% of a fluoride and/or oxide of heavy metal elements. In an example a cement powder is described containing 75 g of calcium tungstate, 25 g of calcium aluminium fluorosilicate glass and 4 g of pyrogenic silicic acid and pigments. The cement powder is mixed with an appropriate cement liquid resulting in a hardened product having a compressive strength of 90 MPa.

DESCRIPTION OF THE INVENTION

It is an object of the present invention to provide a dental cement composition in particular a GIZ, showing adequate or improved physical properties after hardening (like flexural and/or compressive strength) and an improved shelf life during storage, without the need for an expensive secondary packaging or the need for encapsulating moisture sensitive components being present in the composition or the need for desiccants.

It was found that this object can be achieved, if the overall amount of polyacid used for formulating the glass ionomer cement composition is reduced in comparison to commercially available glass ionomer cement compositions used for restorative purposes, in particular, if the polyacid being typically added to the powder part is replaced by a non acid-reactive filler.

In this respect, in one embodiment the present invention features a kit of parts for preparing a glass ionomer cement, the kit comprising a Part A and a Part B Part A being a powder and comprising
an acid-reactive filler in an amount above about 60 wt. %, preferably from 60 to 95 wt. %,
the acid-reactive filler having a mean particle size in the range of 3.5 to 10 µm,
a non acid-reactive filler in an amount above about 1 wt. %, preferably from 5 to 30 wt. %,
the non acid-reactive filler having a mean particle size in the range of 1 to 3.5 µm,
Part A not comprising a polyacid in an amount more than 2.5 or more than 2 or more than 1 wt. %
wt. % with respect to the weight of Part A,
Part B being a liquid and comprising:
a polyacid in an amount above about 30 wt. %, preferably from 35 to 60 wt. %,
water,
a complexing agent,
wt. % with respect to the weight of Part B.

In another embodiment, the invention relates to a process for producing a hardenable composition comprising the step of mixing Part A and Part B of the kit of parts as described in the text of the invention.

Moreover, the invention features a method of using the kit of parts and the cement composition obtainable or being obtained by mixing the liquid and powder component as described in the text for dental purposes, in particular as dental filling material, core build up materials or as root channel filling material.

Unless defined differently, for this description the following terms shall have the given meaning:

A "dental composition" or a "composition for dental use" or a "composition to be used in the dental field" is any composition which can be used in the dental field. In this respect the composition should be not detrimental to the patients' health and thus free of hazardous and toxic components being able to migrate out of the composition. Dental compositions are typically hardenable compositions, which can be hardened at ambient conditions, including a temperature range from about 15 to 50° C. or from about 20 to 40° C. within a time frame of about 30 min or 20 min or 10 min. Higher temperatures are not recommended as they might cause pain to the patient and may be detrimental to the patient's health. Dental compositions are typically provided to the practitioner in comparable small volumes, that is volumes in the range from about 0.1 to about 100 ml or from about 0.5 to about 50 ml or from about 1 to about 30 ml. Thus, the storage volume of useful packaging devices is within these ranges.

A "polymerizable component" is any component which can be cured or solidified e.g. by heating to cause polymerization, chemical crosslinking, radiation-induced polymerization or crosslinking by using a redox initiator. A polymerizable component may contain only one, two, three or more polymerizable groups. Typical examples of polymerizable groups include unsaturated carbon groups, such as a vinyl group being present i.a. in a (methyl)acrylate group.

The cement composition described in the present text does not contain polymerizable components in an amount above about 0.5 or 1 wt.-% with respect to the whole composition. The cement composition described in the present text is essentially free of polymerizable components bearing (meth)acrylate groups.

A "monomer" is any chemical substance which can be characterized by a chemical formula, bearing polymerizable groups (including (meth)acrylate groups) which can be polymerized to oligomers or polymers thereby increasing the molecular weight. The molecular weight of monomers can usually simply be calculated based on the chemical formula given.

As used herein, "(meth)acryl" is a shorthand term referring to "acryl" and/or "methacryl". For example, a "(meth) acryloxy" group is a shorthand term referring to either an acryloxy group (i. e., $CH_2$=CH—C(O)—O—) and/or a methacryloxy group (i. e., $CH_2$=C($CH_3$)—C(O)—O—).

An "initiator" is a substance being able to start or initiate the curing process of polymerizable components or monomers, e.g. redox/auto-cure chemical reaction or by a radiation induced reaction.

A "powder" means a dry, bulk solid composed of a large number of very fine particles that may flow freely when shaken or tilted.

A "particle" means a substance being a solid having a shape which can be geometrically determined Particles can typically be analysed with respect to e.g. grain size or diameter.

The mean particle size of a powder can be obtained from the cumulative curve of the grain size distribution and is defined as the arithmetic average of the measured grain sizes of a certain powder mixture. Respective measurements can be done using commercially available granulometers (e.g. CILAS Laser Diffraction Particle Size Analysis Instrument).

The term "d50/µm" with regard to particle size measurement means that in 50% of the analyzed volume, the particles have a size belowxµm. E.g., a particle size value of below 100 µm (d50) means that within the analyzed volume, 50% of the particles have a size below 100 µm.

"Paste" shall mean a soft, viscous mass of solids dispersed in a liquid. "Viscous" means a viscosity above about 3 Pa*s (at 23° C.).

A "liquid" means any solvent or liquid which is able to at least partially disperse or dissolve a component at ambient conditions (e.g. 23° C.). A liquid typically has a viscosity below about 10 or below about 8 or below about 6 Pa*s.

"Glass ionomer cement" or "GIZ" shall mean a cement curing or hardening by the reaction between an acid-reactive glass and a polyacid in the presence of water.

"Resin modified ionomer cement" or "RM-GIZ" shall mean a GIZ containing in addition polymerizable component(s), an initiator system and typically 2-hydroxyl-ethyl-methacrylate (HEMA).

"Acid-reactive filler" shall mean a filler that chemically reacts in the presence of an acidic component.

"Non acid-reactive filler" shall mean a filler, which does not show a curing reaction within 6 min at all, if mixed with a polyacid or which only shows a reduced (i.e. time-delayed) curing reaction.

To distinguish an acid-reactive filler from a non acid-reactive filler the following test can or is to be conducted:

A composition is prepared by mixing Part A with Part B in a mass ratio of 3.1 to 1, wherein:

Part A contains: filler to be analyzed: 100 wt. %

Part B contains: poly (acrylic acid co maleic acid) (Mw: about 18,000+/−3,000): 43.6 wt. %, water: 47.2 wt. %, tartaric acid: 9.1 wt. %, benzoic acid: 0.1 wt. %.

The filler is characterized as non-acid reactive, if within 6 min after preparing the above composition the shear stress is less than 50,000 Pa, if determined by conducting an oszillating measurement using a rheometer by applying the following conditions: using an 8 mm plate, 0.75 mm gap, at 28° C., frequency: 1.25 Hz, deformation: 1.75%.

Figure 1:
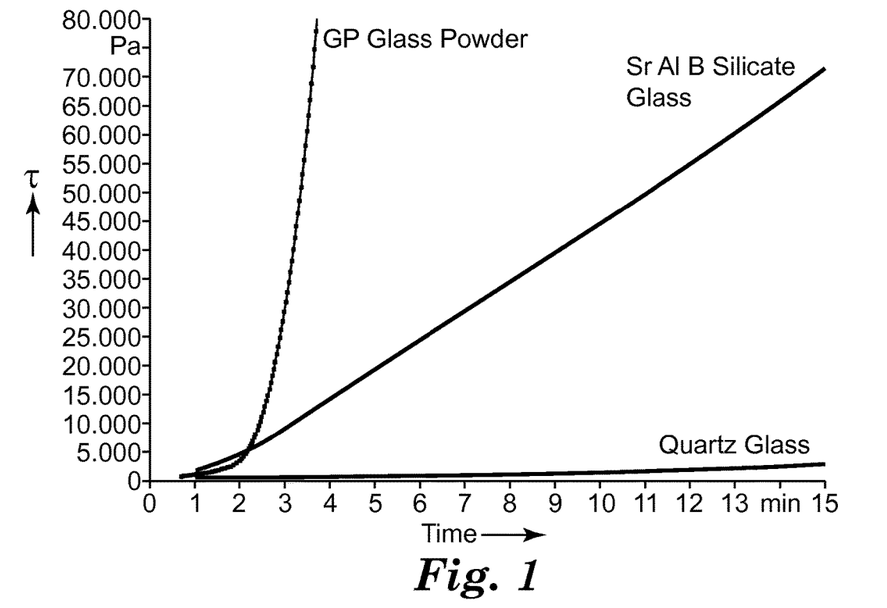
FIG. 1 is a diagram showing the change of shear rate over time, if a particular filler is mixed with a typical GIZ liquid (composition containing polyacrylic acid, water, tartaric acid and benzoic acid).

The different curing behaviour and difference in shear rate, respectively, of an acid-reactive filler (powder component GP glass powder) compared to two non acid-reactive fillers (Sr Al B Silicate Glass or quartz) is demonstrated in FIG. 1. In contrast to the acid-reactive filler the shear rate determined for the non acid-reactive fillers is less steep.

"Cation reduced aluminosilicate glasses" shall mean a glass having a lower content of cations in the surface region of the glass particle compared with the inner region of the glass particle.

These glasses react much slower upon contact with a solution of polyacrylic acid in water as compared to typical acid-reactive filler. Examples of non acid-reactive filler include quartz glass or strontium oxide based glasses. Further examples are given in the text below.

This can be achieved by a surface treatment of the glass particles. Suitable surface treatments include, but are not limited to, acid washing (e.g., treatment with a phosphoric acid), treatment with a phosphate, treatment with a chelating agent such as tartaric acid, and treatment with a silane or an acidic or basic silanol solution.

Desirably the pH of the treating solution or the treated glass is adjusted to neutral or near-neutral, as this can increase storage stability of the composition.

"Polyacid" or "polyalkenoic acid" shall mean a polymer having a plurality of acidic repeating units (e.g. more than 10 or more than 20 or more than 50). That is, the acidic repeating units are attached to or pending from the backbone of the polymer.

"Complexing agent" shall mean a low molecular agent comprising moieties and being able to form a complex with metal ions like calcium or magnesium; e.g. tartaric acid.

A "storage stable composition" is a composition which can be stored for an adequate period of time (e.g. at least about 12 months under ambient conditions) without showing significant performance issues (e.g. reduced flexural or compressive strength and/or which does not harden in the desired period of time (e.g. setting time greater than 6 min)), when used. A suitable test for determining the storage stability is given in the Example section below.

By "hardenable" or "curable" is meant that the composition can be cured or solidified, e.g. by conducting a glass ionomer cement reaction without the need for an additional curing system like chemical cross-linking, radiation-induced polymerization or crosslinking.

A composition is "essentially or substantially free of" a certain component, if the composition does not contain said component as an essential feature. Thus, said component is not wilfully added to the composition either as such or in combination with other components or ingredient of other components.

A composition being essentially free of a certain component usually contains the component in an amount of less than about 1 wt.-% or less than about 0.5 wt.-% or less than about 0.1 wt.-% or less than about 0.01 wt.-% with respect to the whole composition or material. The composition may not contain the said component at all. However, sometimes the presence of a small amount of the said component is not avoidable e.g. due to impurities contained in the raw materials used.

"Ambient conditions" mean the conditions which the inventive composition is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1013 mbar. In the dental and orthodontic field ambient conditions are reasonably understood as a pressure of about 950 to about 1050 mbar, temperature of about 15 to about 40° C. and relative humidity of about 20 to about 80%.

As used herein, "a", "an", "the", "at least one" and "one or more" are used interchangeably. The terms "comprises" or "contains" and variations thereof do not have a limiting meaning where these terms appear in the description and claims. The term "comprising" also includes the more limited expressions "consisting essentially of" and "consisting of".

Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about."

DETAILED DESCRIPTION OF THE INVENTION

The glass ionomer cement (GIZ) described in the present text has a couple of advantageous properties.

Due to formulation of the powder part without polyacid, the glass ionomer cement becomes sufficiently storage stable. That is, there is no need to package either the powder part or the entire kit into a humidity tight or moisture proven foil bag.

Thus, the kit of parts can be stored in a dental capsule (typically made of plastic material) even under severe conditions (humidity above about 95% for 2 months) without noteworthy implications on the physical properties.

Thus, even, if stored under these severe conditions, the physical-mechanical properties of the hardened GIZ are still in the desired range.

This is not only an advantage for the practitioner as the kit of parts is easier to open and apply combined with a reduction in waste, but also for the manufacturer as the kit of parts can be provided without the need for an expensive moisture proven metal coated packaging material.

Maintaining or even improving the desired physical-mechanical properties of the glass ionomer cement, however, cannot be achieved without the addition of a certain amount of non-acid reactive filler to the powder part.

It is surprising that by replacing a portion of a reactive component (i.e. polyacid) by a nearly inert or low reactive component as described in more detail in the present text, the physical-mechanical properties can be maintained or even improved without negatively affecting other properties like setting or mixing behaviour.

It was found that by adding non acid-reactive filler(s) to the powder part of a glass ionomer cement formulation, a high physical-mechanical performance level of the hardened glass ionomer cement can be achieved, without the need to add polyacid in the dry state to the powder part of the glass ionomer cement and without the need for a specific additional secondary moisture proven packaging material.

Thus, the kit of parts and cement composition obtainable by mixing the powder and liquid part of the kit as described in the present text provides a couple of advantageous properties:

a) sufficient flexural strength of the hardened composition, b) improved compressive strength of the hardened composition, c) improved storage stability of the kit of parts, d) by maintaining adequate mixing properties of the powder and liquid part of the kit of parts, and e) by maintaining adequate setting properties of the curable composition obtained by mixing the powder and liquid part.

Further, it has been found that the composition obtained by mixing the individual parts of the kit of parts described in the present text is less sticky to dental instruments than GIZ compositions available on the market. This is in particular advantageous as it allows an easier application of the composition to a tooth cavity and an easy shaping of the applied composition, if desired.

It has been also found that the wear resistance is better compared to commercially available GIZ compositions.

The kit of parts described in the present text thus enables the skilled person to provide a composition having superior mechanical and handling properties.

The cement composition described in the present text comprises a powder part and a liquid part.

Upon mixing those two parts, a curing or hardening composition in the form of a paste is obtained.

According to one embodiment the cement composition obtained or obtainable by mixing the powder and liquid part of the kit of parts described in the present text fulfils at least one or both of the following parameters before or during hardening:

Setting time: within about 5 or 4.5 or 4 min determined according to EN-ISO 9917-1:2007;

Difference in setting time before and after storing the kit of parts for 4 weeks at 23° C. and 95% humidity: less than about 0.5 min.

If desired, the setting time and curing behaviour can be determined as described in more detail in the Example section below. That is, according to one embodiment the cement composition has a consistency and/or viscosity suitable to use the composition as a dental filling material. The cement composition described in the present text has also a sufficient working time allowing the practitioner not only to adequately mix the composition but also to apply the composition to the surface of a crown, bridge, root canal or prepared tooth. Further, the cement composition described in the present text has an adequate setting time, which is time saving for the practitioner and convenient for the patient.

According to another embodiment the cement composition obtained or obtainable by mixing the powder and liquid part of the kit of parts described in the present text fulfils at least one or more, sometimes all of the following parameters after hardening:

Flexural strength: above about 35 or above about 40 MPa determined according to EN-ISO 9917-2:2010 with the proviso that for covering the composition a glass slab is used instead of a foil;

Compressive strength: above about 200 or above about 220 or above about 240 MPa determined according to EN-ISO 9917-1/2007 with the proviso that for covering the composition a glass slab is used instead of a foil;

If desired, these parameters can be determined as described in the Example section below. Compared to state of the art glass ionomer cements available on the market, the cement composition described in the present text has not only a sufficient flexural strength but also an improved compressive strength without affecting other important parameters like working and setting time. The kit of parts described in the present text comprises or consists of two parts, a powder part and a liquid part. The kit of parts may in addition contain an instruction of use. The instruction of use typically contains hints how to store the kit of parts, mix the components of the kit of parts and/or apply and use the composition obtained by mixing the components to the surface of a tooth.

The cement composition described in the present text contains an acid-reactive filler. The nature and structure of the acid-reactive filler is not particularly limited unless the desired result cannot be achieved. The acid-reactive filler has to be able to undergo a glass-ionomer reaction.

According to one embodiment, the acid-reactive filler can be characterized by at least one or more or all of the following parameters:

Mean particle size: about 3.5 to about 10 μm;
(d10/μm): from 0.5 μm to 3 μm; (d50/μm): from 3 μm to 7 μm; (d90/μm): from 6 μm to 15 μm.

If the mean particle size of the acid-reactive filler is above the range outlined above, the consistency of the composition obtained when mixing the compositions contained in the parts of the kit of parts described in the present text will not be adequate and the desired mechanical properties might be negatively affected.

If the mean particle size of the acid-reactive filler is below the range outlined above, the setting time will be too fast.

Suitable acid-reactive fillers include metal oxides, metal hydroxides, acid-reactive glasses. Typical metal oxides include barium oxide, strontium oxide, calcium oxide, magnesium oxide, zinc oxide. Typical metal hydroxides include calcium hydroxide, magnesium hydroxide, strontium hydroxide and mixtures thereof. Typical acid-reactive glasses include aluminosilicate glasses and in particular fluoroaluminosilicate ("FAS") glasses.

FAS glasses are particularly preferred. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, silica, alumina, and other glass-forming ingredients using techniques familiar to those skilled in the FAS glass-making art. The FAS glass typically is in the form of particles that are sufficiently finely divided so that they can conveniently be mixed with the other cement components and will perform well when the resulting mixture is used in the mouth.

Suitable FAS glasses will be familiar to those skilled in the art, and are available from a wide variety of commercial sources, and many are found in currently available glass ionomer cements such as those commercially available under the trade designations KETAC-MOLAR or KETAC-FIL PLUS (3M ESPE Dental Products), and FUJI IX (G-C Dental Industrial Corp., Tokyo, Japan). Fluoroaluminosilicate glasses can be prepared by fusing mixtures of silica, alumina, cryolite and fluorite. Mixtures of acid-reactive fillers can be used, if desired.

Useful acid-reactive glasses can also be characterized by the Si/Al ratio. Fillers having a Si/Al ratio (by wt.-%) of below 1.5 or 1.4 or 1.3 were found to be useful.

Suitable acid-reactive fillers are also commercially available from e.g. Schott AG (Germany) or Speciality Glass (US).

The acid-reactive filler is typically present in the following amounts (wt. % with respect to the weight of Part A):
Lower limit: at least about 10 or at least about 15 or at least about 20 or at least about 30 or at least about 40 or at least about 60 or at least about 65 wt. %;
Upper limit: utmost about 85 or utmost about 75 or utmost about 50 wt. %;
Range: from about 10 to about 85 or from about 15 to about 75 or about 20 to about 50 wt. % or about 60 to about 85 wt. %.

If the amount of the acid-reactive filler is too high, the compositions contained in the parts of the kit of parts described in the present text cannot be adequately mixed, obtaining an adequate consistency and acceptable mechanical properties might become difficult.

If the amount of the acid-reactive filler is too low, a suitable paste cannot be obtained by mixing the respective compositions contained in the parts of the kit of parts described in the present text. Further, the mechanical properties might become inferior.

The cement composition described in the present text contains non acid-reactive filler(s). A non acid-reactive filler is a filler, which either does not cure in a glass ionomer reaction at all, if combined with a polyacid in the presence of water, or only shows a delayed curing reaction.

A more precise definition of non acid-reactive filler is given above. The nature and structure of the non acid-reactive filler is not particularly limited, either unless the desired result cannot be achieved. The non-acid reactive filler is preferably an inorganic filler. The filler should be non-toxic and suitable for use in the mouth of a human being. The filler can be radiopaque or radiolucent. The filler typically is substantially insoluble in water. "Insoluble in water" means that less than about 1 or 0.5 or 0.1 wt.-% of filler dissolves in water, if 10 g filler is stirred in 100 ml water for 1 month.

According to one embodiment, the non acid-reactive filler can be characterized by at least one or more or all of the following parameters:
Mean particle size: about 1 to about 3.5 µm
(d10/µm): from 0.1 µm to 0.5 µm; (d50/µm): from 0.5 µm to 3 µm; (d90/µm) from 1 µm to 6 µm;
Solubility: substantially insoluble in water.

If the mean particle size of the non acid-reactive filler is above the range outlined above, the consistency of the obtained paste might not be adequate and the desired mechanical properties cannot be obtained.

If the mean particle size of the non acid-reactive filler is below the range outlined above, the desired consistency of the obtained paste might not be adequate.

Examples of suitable non acid-reactive fillers are naturally occurring or synthetic materials including, but not limited to: quartz; nitrides (e.g., silicon nitride); glasses derived from, e.g., Zr, Sr, Ce, Sb, Sn, Ba, Zn, and Al; feldspar; borosilicate glass; kaolin; talc; cation reduced aluminosilicate glasses (sometimes also referred to as cation depleted glasses), silica particles (e.g., submicron pyrogenic silicas such as those available under the trade designations AEROSIL, including "OX 50," "130," "150" and "200" silicas from Degussa AG, Hanau, Germany and HDK, including "H15", "H20", "H2000" from Wacker, Munich, Germany, and CAB-O-SIL M5 silica from Cabot Corp., Tuscola, Ill.), alumina and zirconia particles.

Useful non acid-reactive fillers can also be characterized by the Si/Al ratio. Fillers having a Si/Al ratio (by wt.-%) of above or equal to 1.5 or 1.7 or 2.0 were found to be useful. Mixtures of these non-acid-reactive fillers are also contemplated. Suitable non acid-reactive fillers are also described in the following documents: U.S. Pat. No. 4,376,835 (Schmitt et al.). The content of these documents with respect to the description of the non acid-reactive filler is herewith incorporated by reference. Suitable non acid-reactive fillers are also commercially available from e.g. Schott (Germany) or Speciality Glass (US).

If desired, the surface of the non acid-reactive filler particles can be surface treated as described in this text with respect to the acid-reactive filler(s).

The non acid-reactive filler is typically present in the following amounts (with respect to the weight of the overall composition):
Lower limit: at least about 1 or at least about 3 or at least about 10 wt. %;
Upper limit: utmost about 50 or utmost about 40 or utmost about 30 wt. %;
Range: from about 1 to about 50 or from about 3 to about 40 or from about 10 to about 30 wt. %.

The cement composition described in the present text contains polyacid(s). The nature and structure of the polyacid is not particularly limited, either, unless the desired result cannot be achieved. However, the polyacid should have a molecular weight sufficient to provide good storage, handling, and mixing properties.

According to one embodiment, the polyacid can be characterized by at least one or more or all of the following parameters:
Being a solid (at 23° C.);
Molecular weight (Mw): from about 2,000 to about 250,000 or from about 5,000 to about 100,000 (evaluated against a polyacrylic acid sodium salt standard using gel permeation chromatography).

If the molecular weight of the polyacid is too high, obtaining a workable consistency of the obtained paste when mixing the compositions contained in the parts of the kit of parts described in the present text might become difficult. Further mixing of the compositions might become difficult. In addition the obtained mixture or composition might become too sticky (i.e. adheres to the dental instrument used for application).

If the molecular weight of the polyacid is too low, the viscosity of the obtained paste might become too low and the mechanical properties inferior. Typically, the polyacid is a polymer having a plurality of acidic repeating units. The polyacid to be used for the cement composition described in the present text is substantially free of polymerizable groups. The polyacid need not be entirely water soluble, but typically it is at least sufficiently water-miscible so that it does not undergo substantial sedimentation when combined with other aqueous components.

The polyacid is hardenable in the presence of, for example, an acid-reactive filler and water, but does not contain ethylenically unsaturated groups. That is, it is a polymer obtained by polymerising an unsaturated acid. However, due to the production process, a polyacid might still contain traces of free monomers (e.g. up to about 1 or 0.5 or 0.3 wt. % with respect to the amount of monomers used).

Typically, the unsaturated acid is an oxyacid (i.e., an oxygen containing acid) of carbon, sulfur, phosphorous, or boron. More typically, it is an oxyacid of carbon. Suitable polyacids include, for example, polyalkenoic acids such as homopolymers and copolymers of unsaturated mono-, di-, or tricarboxylic acids.

Polyalkenoic acids can be prepared by the homopolymerization and copolymerization of unsaturated aliphatic carboxylic acids, e.g., acrylic acid, methacrylic acid, itaconic acid, maleic acid, glutaconic acid, aconitic acid, citraconic acid, mesaconic acid, fumaric acid, and tiglic acid.

Suitable polyacids also include alternating copolymers of maleic acid and ethylene (e.g. in a one to one ratio). Suitable polyacids are also described in the following documents: U.S. Pat. No. 4,209,434 (Wilson et al.), U.S. Pat. No. 4,360,605 (Schmitt et al.). The content of these documents with respect to the description of the polyacid is herewith incorporated by reference. Suitable polyacids dissolved in water are also commercially available from e.g. 3M ESPE (e.g. Ketac™ Fil Plus Handmix) or GC Company (e.g. Fuji™ IX GP Handmix)

The amount of polyacid should be sufficient to react with the acid-reactive filler and to provide an ionomer composition with desirable hardening properties.

The polyacid is typically present in the following amounts (wt. % with respect to the weight of the whole composition obtained when mixing the compositions contained in the kit of parts):
Lower limit: at least about 1 or at least about 3 or at least about 5 wt. %;
Upper limit: utmost about 50 or utmost about 40 or utmost about 30 wt. %;
Range: from about 1 to about 50 or from about 3 to about 40 or from about 5 to about 30 wt. %.

If the amount of the polyacid is too high, obtaining a workable consistency of the obtained paste when mixing the compositions contained in the parts of the kit of parts described in the present text might become difficult. Further mixing of the compositions might become difficult. In addition the obtained mixture or composition might become too sticky (i.e. adheres to the dental instrument used for application).

If the amount of the polyacid is too low, obtaining a workable consistency of the obtained paste when mixing the compositions contained in the parts of the kit of parts described in the present text might become difficult, either. Further, it will become difficult to achieve the desired mechanical properties.

The cement composition described in the present text contains water. The water can be distilled, de-ionized, or plain tap water. Typically, deionized water is used. The amount of water should be sufficient to provide adequate handling and mixing properties and to permit the transport of ions, particularly in the filler-acid reaction.

The water is typically present in the following amounts (wt. % with respect to the weight of the whole composition obtained when mixing the compositions contained in the kit of parts):
Lower limit: at least about 5 or at least about 7 or at least about 9 wt. %;
Upper limit: utmost about 16 or utmost about 14 or utmost about 12 wt. %;
Range: from about 5 to about 16 or from about 7 to about 14 or from about 9 to about 12 wt. %.

If the amount of the water is too low, obtaining a workable consistency of the obtained paste when mixing the compositions contained in the parts of the kit of parts described in the present text might become difficult. Further mixing of the compositions might become difficult If the amount of water is too high, obtaining a workable consistency of the obtained paste when mixing the compositions contained in the parts of the kit of parts described in the present text might become difficult, either. Further, it will become difficult to achieve the desired mechanical properties.

The nature and structure of the complexing or chelating agent is not particularly limited, either unless the desired result cannot be achieved.

The complexing agent can be characterized by at least one or more or all of the following parameters:
Solubility: soluble in water (at least about 50 g/l water at 23° C.);
Molecular weight: from about 50 to about 500 g/mol, or from about 75 to about 300 g/mol.

Specific examples of the complexing agent include tartaric acid, citric acid, ethylene diamine tetra acetic acid (EDTA), salicylic acid, mellitic acid, dihydroxy tartaric acid, nitrilotriacetic acid (NTA), 2,4 and 2,6 dihydroxybenzoic acid, phosphono carboxylic acids, phosphono succinic acid and mixtures thereof Further examples can be found e.g. in U.S. Pat. No. 4,569,954 (Wilson et al.). The content of this document is herewith incorporated by reference. The complexing agent is typically added to that part containing the polyacid only.

The complexing agent is typically present in the following amounts (wt. % with respect to the weight of the whole composition obtained when mixing the compositions contained in the kit of parts):
Lower limit: at least about 0.5 or at least about 1.0 or at least about 1.5 wt. %;
Upper limit: utmost about 4.0 or utmost about 5 or utmost about 6 wt. %;
Range: from about 0.5 to about 6.0 or from about 1.0 to about 5 or from about 1.5 to about 4.0 wt. %.

Either Part A or Part B or Part A and Part B of the kit of parts described in the present text can also contain additional components or additives. These components include solvents, co-solvent(s) or diluents(s). Adding solvent(s) or co-solvent(s) may help to adjust the viscosity and consistency of the composition. If desired, the cement composition described in the present text can contain additives such as indicators, dyes, pigments, viscosity modifiers, wetting agents, surfactants, buffering agents, stabilizers, preservative agents (e.g., benzoic acid).

Combinations of any of the above additives may also be employed. The selection and amount of any one such additive can be selected by one of skill in the art to accomplish the desired result without undue experimentation.

There is no need for those component(s) to be present, however, if they are present the individual component is typically present in an amount of less than about 5 wt. % or less than about 3 wt. % or less than about 1 wt. % with respect to the weight of the whole composition.

Useful ranges the further component(s) include from about 0.01 to about 5 wt. % or from about 0.05 to about 3 wt. % or from about 0.1 to about 1 wt. %, wt. % with respect to the weight of the whole composition.

Typically neither Part A nor Part B or nor Part A and Part B of the kit of parts described in the present text do contain either of the following components alone or in combination in an amount above about 1 wt. % or above about 0.5 wt. % with respect to each of the component(s) listed:
a) HEMA,
b) polymerizable component(s),
c) initiator component(s) suitable to cure polymerizable component(s) or monomer(s),
d) desiccant(s) like zeolithe(s),
e) apatite or hydroxyl apatite,
f) inhibitior(s) like methoxyphenol or 3,5-Di-tert-butyl-4-hydroxytoluol.

Thus, the composition obtained when mixing the powder and liquid part of the kit of parts described in the present text is not a so-called resin-modified glass ionomer cement (RM-GIZ) and thus does not contain a chemically or light curing system.

In particular, the cement composition described in the present text does not contain a redox-initiator system or a radiation induced initiator system.

In particular the cement composition described in the present text does not contain the following components:
(a) and (b),
(b) and (c),
(a), (b) and (c),
(b), (c) and (e),
(a), (b), (c) and (f)
in an amount above about 1 wt. % or above about 0.5 wt. % or above about 0.1 wt. % with respect to the weight of the whole composition.

That is, the cement composition described in the present text is typically essentially free of either of these components alone or in combination.

The powder part and the liquid part of the kit of part described in the present text can be produced by simply mixing the individual components of the respective parts. If needed, the filler particles can be milled to the desired particle size using equipment known to the skilled person like ball mills. Mixing can be accomplished either by hand or with a mechanical device like a mixer.

The kit of parts described in the present text can be provided to the practitioner in different embodiments. The powder part and liquid part may be contained in separate sealable vessels (e.g. made out of plastic or glass). For use, the practitioner will take adequate portions of the powder and liquid component from the vessels and mix the portions by hand on a mixing plate. According to a preferred embodiment, the powder part and liquid part are contained in separate compartments of a dental capsule. The dental capsule is activated by using a mechanism which brings the powder part and the liquid part together. Different mechanisms are known in the art. The dental capsule is then typically placed in a device which facilitates the mixing process.

Suitable dental capsules typically contain the following parts or elements: preferably cylindrical container element, nozzle, piston guided in the container element, reservoir for liquid, reservoir for powder, activating means suitable for opening either the reservoir for the liquid or the reservoir for the powder. Suitable dental capsules are also described in the art: U.S. Pat. No. 6,543,611, US 2004/0192433, U.S. Pat. No. 4,941,751, EP 0 783 872 A2. The content of these references is herewith incorporated by reference. Due to the particular formulation of the kit of parts described in the present text, for storage stability reasons there is no need to store either the vessels or the dental capsule in a special pouch or blister. Due to the absence of the polyacid from the powder part, the powder part is sufficient storage stable.

In particular, for storage stability reasons there is no need to store or package the kit of parts in either of the following materials: humidity tight or moisture tight proven foils or blisters (e.g. alumina type blisters) or combinations thereof The composition obtained or obtainable when mixing the respective powder and liquid part is in particular useful as filling material, core build up material or as root channel filling material.

A typical application comprises the following steps:
a) mixing Part A and Part B to obtain a mixture,
b) applying the mixture to the surface of hard dental tissue.

In one embodiment, the kit of parts described in the present text is described as follow:
Part A being a powder and comprising
an acid-reactive filler in an amount from about 10 to about 95 wt %,
  the acid-reactive filler being selected from fluoro alumina silicate glasses and mixtures thereof,
  the acid-reactive filler having a mean particle size in the range of 3.5 to 10 µm,
a non acid-reactive filler in an amount from about 5 to about 30 wt. %,
  the non acid-reactive filler being selected from quartz, strontium boron silicate glasses, barium silicate glasses and mixtures thereof,
  the non acid-reactive filler having a mean particle size in the range of 1 to 3.5 µm,
wt % with respect to the weight of Part A,
Part B being a liquid and comprising
a polyacid in an amount from about 30 to about 60 wt. %,
  the polyacid being selected from poly-acrylic acid, poly-maleic acid, poly-(acrylic acid co-maleic acid), poly-itaconic acid, poly-(acrylic acid co-itaconic acid) and mixtures thereof,
water in an amount from about 30 to about 70 wt %
an acidic complexing agent in an amount from about 1 to about 20 wt %,
  the acidic complexing agent being selected from tartaric acid, hydroxybutanedioic acid, aldaric acid, phosphono succinic acid and mixtures thereof,
wt % with respect to the weight of Part B,
wherein Part A is contained in a Compartment A, and wherein Part B is contained in a Compartment B.

Compartment A and Compartment B being optionally parts of a dental capsule not being packaged in a metal coated foil or blister during storage.

All components used in the dental composition of the invention should be sufficiently biocompatible, that is, the composition should not produce a toxic, injurious, or immunological response in living tissue.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate, but not limit, the scope of this invention. Unless otherwise indicated, all parts and percentages are by weight.

EXAMPLES

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar).
Measurements
Compressive Strength (CS)

Measurement of the compressive strength was carried out according to the EN-ISO 9917-1:2007 with the proviso that for covering the composition a glass slab is used instead of a foil;

Cylindrical specimens with a diameter of 4 mm and a height of 6 mm were used. Specimens of the materials were prepared at room temperature and 50% relative humidity using split moulds. The moulds were placed on microscope slides and thoroughly filled with the mixed material to avoid incorporation of air bubbles. The filled moulds were immediately covered with another glass slab and fixed in a screw clamp with slight pressure to extrude excess material. The whole assembly was stored at 36° C. and at least 95% relative humidity. 1 h after start of mixing the specimens were removed from the moulds and immediately placed in water at 36° C. 6 specimens were prepared for each material. Materials were measured 24 h after start of mixing. The exact diameter of each specimen was measured prior to the measurement. The strength of the specimen was measured by applying a compressive load using a Zwick universal testing machine (Zwick GmbH & Co. KG, Ulm, Germany) operating at a crosshead speed of 1 mm/min. Results were reported as an average of 6 replications.
Flexural Strength (FS)

Flexural strength was measured based on EN ISO 9917-2:2010 with the proviso that for covering the composition a glass slab is used instead of a foil;

The specimens were prepared as described for the compressive strength test above, except that rectangular-shaped split moulds with dimensions 25 mm×2 mm×2 mm were used to prepare the samples. The specimens were subjected to a 3 point bend on supports 20 mm apart at a crosshead speed of 1 mm/min.

Storage Stability

Storage stability was determined according to the following process:

The samples were stored for a given period of time under the following conditions: more than 95% relative humidity at 23° C. After storage the samples were analyzed for mechanical performance (e.g. setting behaviour).
Particle Size If desired, the particle size can be determined with a Cilas 1064 (FA. Quantacrome) particle size detection device.
Molecular Weight If desired, the molecular weight (Mw) can be determined by gel permeation chromatography (GPC) against a polyacrylic acid sodium salt standard.

In particular the following equipment was found to be useful: PSS SECurity GPC System equipped with 2*PSS Suprema 3000A, 8*300 mm, 10 µm columns; eluent: 84 mM Na2HPO4 +200 ppm NaN3; flux rate: 1 ml/min.
Setting Time (STa)

The setting behaviour of the prepared glass ionomer cement composition was determined using a Physica MCR 301 Rheometer (Anton Paar) applying the following parameters:

Oscillating measurement with 8 mm disc on disc set-up; gap 0.75 mm; deformation 1.75%; frequency: 1.25 HZ; temperature: 28° C.

The loss angle (in German: "Verlustwinkel") is recorded over time and the maximum of the graph determined The average of two measurements with respect to the maximum is given in min:sec.

Figure 2:
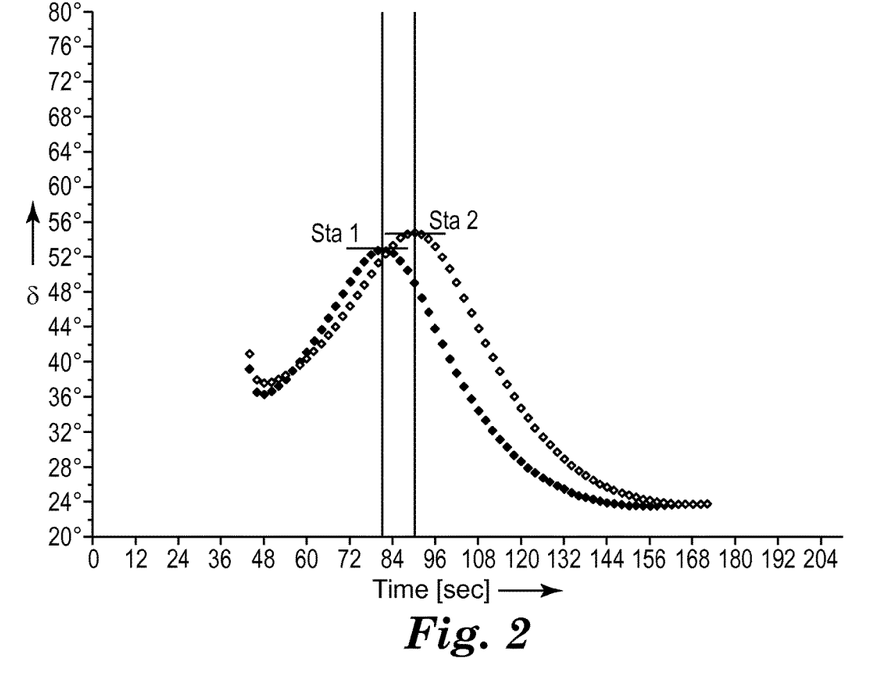
FIG. 2 is a diagram showing the setting behaviour of a GIZ composition with respect to change of loss-angle over time.

An example of a graph showing the setting behaviour with respect to change of loss-angle over time is given in FIG. 2. Each graph represents one measurement and each graph has one maximum (STa(1) and STa(2)).
Materials Used

TABLE 1

| Name | Description | Abbreviation |
|---|---|---|
| Glass powder | acid-reactive filler; mean particle size: 4.8 µm with the following elemental composition: Si: 10-15 wt. %; Al: 10-15 wt. %; Sr: 23-26.5 wt. %; Na: 2.0-4.0 wt. %; F: 11.0-14.5 wt. %; P: 2-3.5 wt. %; La: 4.5-7 wt. %; O: 26-30 wt. % (based on X-Ray Fluoresence Analysis). The acid-reactive filler is made by melting a glass frit, subsequently crushing and grinding the frit to particle size of 4.8 µm, followed by washing with an hydrochloric acid (1 mol/l) for 1 h, filtering, drying and tempering at 200-300° C. for 12 h. | GP |
| Sr Al B silicate glass | non acid-reactive; Al2O3: 15 wt. %; B2O3: 15 wt. %; SrO: 20 wt. %; BaO: 1 wt. %; SiO2: 50 wt. % | |
| Quartz powder | non acid-reactive; mean particle size: 1.0 µm | QA1 |
| Quartz powder | non acid-reactive; mean particle size: 3.8 µm | QA2 |
| Silica powder | non acid-reactive; mean particle size: <0.1 µm | SP |
| Tartaric acid | complexing agent | TA |
| Benzoic acid | stabilizer | BA |
| Poly (acrylic acid co-maleic acid)—Mw: about 18,000 +/− 3,000 | polyacid | PAS |

Compositions I
The following kits of parts were prepared:
Part A (Powder)
(The amounts are given in wt. %.)

|     | A1 | A2 | A3 | A4 | A5 | A6 | A7 |
|-----|----|----|----|----|----|----|----|
| GP  | 75 | 80 | 80 | 95 | 90 | 85 | 80 |
| QA1 |    |    |    | 5  | 10 | 15 | 20 |
| QA2 | 20 | 20 |    |    |    |    |    |
| SP  |    |    | 20 |    |    |    |    |
| PAS | 5  |    |    |    |    |    |    |

Part B (Liquid)
(The amounts are given in wt. %.)
PAS: 43.6; Water: 47.2; BA: 0.1; TA: 9.1
Part B (Liquid) was sealed in an aluminium coated foil bag/blister.
Part A (Powder) was placed in the mixing chamber of a mixing capsule from 3M ESPE (GP glass powder).
Both parts were assembled to a dental mixing capsule. The dental mixing capsule was stored at 23° C. and >95% humidity for 2 weeks, 1 month and 2 months, respectively, without using a humidity tight foil.
After storage, the capsule was activated using a commercially available activator device and the liquid part combined with the powder part (powder/liquid ratio: 3.1 to 1). The mixing capsule was placed in a commercially available mixing device (Capmix™; 3M ESPE) and mixed for 10 sec.
Analysis
The obtained mixture (M) was dispensed from the mixing capsule using a commercially available applicator into a mould for further analysis with respect to its setting time (STa).

|              | Sample |        |        |        |        |        |        |
|--------------|--------|--------|--------|--------|--------|--------|--------|
| Storage time | M-A1 (CE1) | M-A2 (CE2) | M-A3 (CE3) | M-A4 (IE1) | M-A5 (IE2) | M-A6 (IE3) | M-A7 (IE4) |
| Start        | 1:36   | n.m.   | n.m.   | 1:15   | 1:18   | 1:27   | 1:30   |
| 2 weeks      | 1:30   | n.m.   | n.m.   | 1:12   | 1:18   | 1:24   | 1:27   |
| 1 month      | 1:12   | n.m.   | n.m.   | 1:00   | 1:12   | 1:21   | 1:27   |
| 2 months     | n.m.   | n.m.   | n.m.   | 1:15   | 1:15   | 1:24   | 1:27   |

Table: Setting times STa [min:sec]
"n.m."=not measurable; composition cannot be dispensed from the capsule What can be seen is:
- The setting time (STa) for composition M-A1 accelerates over time. After 2 months storage, the composition cannot be dispensed from the dental capsule anymore.
- If the particle size of the filler used is either too high or too low (cf. M-A2, M-A3), the obtained mixture cannot be mixed and dispensed from the dental capsule anymore.
- If the fillers according to the invention are used, the setting time (STa) is fairly constant over time, even if the parts of the composition were stored under severe conditions before mixing.

Compositions II
The following compositions were analyzed with respect to their physical properties:

|   | Product | | | |
|---|---|---|---|---|
|   | Ketac™ Molar Aplicap™ (3M ESPE) | Ketac™ Fil Plus Aplicap™ (3M ESPE) | Fuji™ IX GP (GC) | Chemfil™ Rock (Dentsply) |
| Powder | Poly (acrylic acid co maleic acid); GI glass powder | GI glass powder 100% (acc. to MSDS) | Fluoro alumino-silicate glass 90-100% (acc. To MSDS); Polyacrylic acid 5-10% (acc. to MSDS) | Calcium-aluminum-zinc-fluoro-phosphor-silicate glass (acc. Instructions for use); Poly carboxylic acid 10-25% (acc. to MSDS) |
| Liquid | Poly (acrylic acid co maleic acid); water; tartaric acid; benzoic acid | Poly (acrylic acid co maleic acid); water; tartaric acid; benzoic acid | Polyacrylic acid 30-40% (acc. to MSDS) | Poly carboxylic acid 10-25%; L-(+)-Tartaric acid (acc. to MSDS) |
| FS [MPa] | 51.7 ± 8.9 | 35.8 ± 3.1 | 48.3 ± 3.5 | 67.2 ± 6.7 |
| CS [MPa] | 246.1 ± 17.5 | 177.8 ± 24.9 | 216.2 ± 16.8 | 181.6 ± 6.9 |
| Secondary packaging of dental capsule | Aluminium based foil; humidity tight | Plastic based foil; no humidity protection needed | Aluminium based foil; humidity tight | Aluminium based foil; humidity tight |

|   | Product | | |
|---|---|---|---|
|   | Ionofil™ Molar (Voco) | Example 1 | Example 2 |
| Powder | Polyacrylic acid 2.5-5%; silicium dioxide 2.5-5%; L-Tartaric acid 2.5-5% (acc. to MSDS) | GP 80%; QA1 20% | GP 80%; Sr Al B silicate glass powder 20% |
| Liquid | Polyacrylic acid solution 50-100% (acc. to MSDS) | Poly (acrylic acid co maleic acid) 43.6%; water 47.2%; tartaric acid 9.1%; benzoic acid 0.1% | Poly (acrylic acid co maleic acid) 43.6%; water 47.2%; tartaric acid 9.1%; benzoic acid 0.1% |

-continued

| | Product | | |
|---|---|---|---|
| | Ionofil ™ Molar (Voco) | Example 1 | Example 2 |
| FS [MPa] | 54.8 ± 6.8 | 52.1 ± 5.5 | 46.4 ± 1.8 |
| CS [MPa] | 201.5 ± 16.6 | 271.5 ± 20.9 | 241.0 ± 18.7 |
| Secondary packaging of dental capsule | Aluminium based foil; humidity tight | Plastic based foil; no humidity protection needed | Plastic based foil; no humidity protection needed |

What can be seen is:

The mechanical properties like compressive strength determined for the compositions according to the invention are better than the respective values determined for commercialized glass ionomer compositions. Further, compared to the commercially available glass ionomer products, the composition according to the invention can be stored without the need of a humidity tight secondary packaging.

What is claimed is:

1. A kit of parts for preparing a glass ionomer cement for dental use, the kit comprising a Part A and a Part B,
    Part A being a powder and comprising:
    an acid-reactive inorganic filler in an amount from above about 60 to about 95 wt. %,
    the acid-reactive filler having a mean particle size in the range of 3.5 to 10 µm,
    an non acid-reactive inorganic filler in an amount above about 5 to about 30 wt. %,
    the non acid-reactive filler having a mean particle size in the range of 1.0 to 3.5 µm,
        Part A not comprising a polyacid in an amount above about 1 wt. %,
    wt. % with respect to the weight of Part A, and
    Part B being a liquid and comprising:
    a polyacid in an amount above about 35 to about 60 wt. %, wt. %, with respect to the weight of
    Part B,
    water,
    a complexing agent.

2. The kit of claim 1, wherein both of Part A and Part B do not comprise an amount above about 1 wt. % with respect to the weight of the glass ionomer cement of any of the following components:
    HEMA,
    polymerizable component(s),
    initiator component(s) suitable to cure polymerizable component(s) or monomer(s),
    desiccant(s),
    apatite or hydroxyl apatite, and
    inhibitior(s).

3. The kit of claim 1, the acid-reactive inorganic filler being selected from basic metal oxides, metal hydroxides, aluminosilicate glasses, glasses having a Si/Al ratio by wt.-% of below 1.5 and mixtures thereof.

4. The kit of claim 1, the non acid-reactive inorganic filler being selected from quartz, nitrides, silica, kaolin, feldspar, borosilicate glass, strontium oxide based glass, barium oxide based glass, cation reduced aluminosilicate glasses, glasses having a Si/Al ratio by wt.-% of above or equal to 1.5 and mixtures thereof.

5. The kit of claim 1, the polyacid being selected from homopolymers and copolymers of acrylic acid, methacrylic acid, itaconic acid, maleic acid, glutaconic acid, aconitic acid, citraconic acid, mesaconic acid, fumaric acid, tiglic acid, copolymers of maleic acid and ethylene and mixtures thereof.

6. The kit of claim 1, the complexing agent being selected from tartaric acid, citric acid, ethylene diamine tetra acetic acid (EDTA), salicylic acid, mellitic acid, dihydroxy tartaric acid, nitrilotriacetic acid (NTA), 2,4 and 2,6 dihydroxybenzoic acid, phosphono carboxylic acids, phosphono succinic acid and mixtures thereof.

7. The kit of claim 1,
    either Part A or Part B or Part A and Part B comprising in addition one or more of the following components: solvent(s), indicator(s), dye(s), pigment(s), viscosity modifier(s), wetting agent(s), surfactant(s), buffering agent(s), stabilizer(s), preservative agent(s), solvent(s) or mixtures thereof.

8. The kit of claim 1, the weight ratio of Part A to Part B being from 2:1 to 4:1.

9. The kit of claim 1,
    Part A being contained in a Compartment A,
    and Part B being contained in a Compartment B,
    Compartment A and Compartment B being parts of a dental capsule, the dental capsule not being packaged in a humidity tight packaging material.

10. The kit of claim 1,
    Part A being a powder and comprising:
    an acid-reactive filler in an amount from about 10 to about 95 wt %,
    the acid-reactive inorganic filler comprising fluoro alumina silicate glass,
    the acid-reactive inorganic filler having a mean particle size in the range of 3.5 to 10 µm,
    a non acid-reactive inorganic filler in an amount from about 5 to about 30 wt %
    the non acid-reactive inorganic filler being selected from quartz, strontium boron silicate glasses, barium silicate glasses and mixtures thereof,
    the non acid-reactive inorganic filler having a mean particle size in the range of 1 to 3.5 µm,
    wt% with respect to the weight of Part A,
    Part B being a liquid and comprising:
    a polyacid in an amount from about 30 to about 60 wt %,
    the polyacid being selected from poly-acrylic acid, poly-maleic acid, poly-(acrylic acid co-maleic acid), poly-itaconic acid, poly-(acrylic acid co-itaconic acid) and mixtures thereof,
    water in an amount from about 30 to about 70 wt %,
    an acidic complexing agent in an amount from about 1 to about 20 wt %,
    the acidic complexing agent being selected from tartaric acid, hydroxybutanedioic acid, aldaric acid, phosphono succinic acid and mixtures thereof,
    wt% with respect to the weight of Part B,
    wherein Part A is contained in a Compartment A, and wherein Part B is contained in a Compartment B.

11. A process for preparing a hardenable composition for dental use, the composition of claim 1, the process comprising the step of mixing Part A and Part B.

12. A hardenable or hardening composition for dental use produced by mixing Part A and Part B of the kit of parts of claim 1, the composition being characterized by at least one or more of the following parameters:
    Setting time: within about 5 min determined according to ISO 9917:1/2007; and
    Difference in setting time before and after storing the kit of parts for 4 weeks at 23° C. and 95% humidity: less than about 0.5 min.

13. A hardened composition for dental use, comprising a composition produced by a process comprising mixing Part A and Part B of the kit of parts of claim 1,
   the hardened composition being characterized by at least one or more of the following parameters:
   Flexural strength: above about 35 MPa determined according to EN-ISO 9917-2:2010; and
   Compressive strength: above about 200 MPa determined according to EN-ISO 9917-1/2007.

14. Use of the composition of claim 13 by mixing Part A and Part B for preparing a dental filling material, core build up material or root channel filling material.

15. Use of the kit of parts of claim 1 by mixing Part A and Part B for preparing dental filling material, core build up material or root channel filling material.

16. The hardenable or hardening composition for dental use of claim 12, wherein the Setting time is within about 4.5 min determined according to ISO 9917:1/2007.

17. The hardenable or hardening composition for dental use of claim 12, wherein the Setting time is within about 4.0 min determined according to ISO 9917:1/2007.

18. The hardened composition for dental use of claim 13, wherein the Compressive strength is above about 220 MPa determined according to EN-ISO 9917-1/2007.

19. The hardened composition for dental use of claim 13, wherein the Compressive strength is above about 240 MPa determined according to EN-ISO 9917-1/2007.

20. The hardened composition for dental use of claim 13, wherein the Flexural strength is above about 40 MPa determined according to EN-ISO 9917-2:2010.

\* \* \* \* \*

UNITED STATES PATENT AND TRADEMARK OFFICE
CERTIFICATE OF CORRECTION

PATENT NO. : 10,080,708 B2
APPLICATION NO. : 15/102483
DATED : September 25, 2018
INVENTOR(S) : Robert Peez It is certified that error appears in the above-identified patent and that said Letters Patent is hereby corrected as shown below:

In the Specification

Column 4
Line 34, Delete "(i. e.,$CH_2$" and insert -- (i. e., $CH_2$ --, therefor.

Column 4
Line 35, Delete "(i. e.," and insert -- (i.e., --, therefor.

Column 5
Line 22, Delete "oszillating" and insert -- oscillating --, therefor.

Column 8
Line 30, Delete "foil;" and insert -- foil. --, therefor.

Column 11
Line 49, Delete "Handmix)" and insert -- Handmix). --, therefor.

Column 12
Line 30, Delete "difficult" and insert -- difficult. --, therefor.

Column 12
Line 51, Delete "thereof" and insert -- thereof. --, therefor.

Column 13
Line 34, Delete "inhibitior(s)" and insert -- inhibitor(s) --, therefor.

Column 14
Line 28, Delete "thereof" and insert -- thereof. --, therefor.

Signed and Sealed this
Seventh Day of May, 2019

Andrei Iancu
*Director of the United States Patent and Trademark Office*

CERTIFICATE OF CORRECTION (continued)
U.S. Pat. No. 10,080,708 B2

Column 16
Line 10 (approx.), Delete "Quantacrome)" and insert -- Quantachrome) --, therefor.

Column 16
Line 48 (approx.), Delete "determined" and insert -- determined. --, therefor.

In the Claims

Column 19
Line 54, In Claim 2, delete "inhibitior(s)." and insert -- inhibitor(s). --, therefor.

Column 20
Line 18, In Claim 8, delete "2: 1" and insert -- 2:1 --, therefor.

Column 20
Line 29, In Claim 10, after "comprising" insert -- a --.